United States Patent
Das

(10) Patent No.: US 11,628,124 B2
(45) Date of Patent: Apr. 18, 2023

(54) FEEDING TUBE MANAGEMENT

(71) Applicant: Silviya Das, Ontario, CA (US)

(72) Inventor: Silviya Das, Ontario, CA (US)

( * ) Notice: Subject to any disclaimer, the term of this patent is extended or adjusted under 35 U.S.C. 154(b) by 0 days.

(21) Appl. No.: 17/243,318

(22) Filed: Apr. 28, 2021

(65) Prior Publication Data
US 2022/0347059 A1    Nov. 3, 2022

(51) Int. Cl.
*A61J 15/00* (2006.01)
*A61M 39/10* (2006.01)
*A61M 1/00* (2006.01)

(52) U.S. Cl.
CPC ....... *A61J 15/0026* (2013.01); *A61J 15/0003* (2013.01); *A61J 15/0092* (2013.01); *A61M 1/81* (2021.05); *A61M 39/10* (2013.01); *A61M 2039/1083* (2013.01)

(58) Field of Classification Search
CPC .. A61J 15/003; A61J 15/0015; A61J 15/0026; A61J 15/0092; A61M 2039/085; A61M 2039/1083; A61M 39/10; A61M 2039/1077; A61M 3/223; A61M 39/24; A61M 39/223; A61M 1/2089; A61M 1/2093; A61M 15/0026; A61M 15/0092; A61M 1/2003
See application file for complete search history.

(56) References Cited

U.S. PATENT DOCUMENTS

| 4,895,562 A | * | 1/1990 | Lopez | A61M 39/223 604/48 |
| 5,071,405 A | * | 12/1991 | Piontek | A61J 15/0042 604/910 |
| 5,217,442 A | * | 6/1993 | Davis | A61M 5/14276 604/218 |

(Continued)

FOREIGN PATENT DOCUMENTS

| JP | 2019502458 A | 1/2019 |
| KR | 20110067023 A | 6/2011 |

(Continued)

OTHER PUBLICATIONS

Simply03, https://www.simplyo3.com/products/3-way-valve.
Vet, https://www.thevetstore.net/shop/3-way-stop-cock/.

*Primary Examiner* — Nathan R Price
*Assistant Examiner* — Melissa A Snyder
(74) *Attorney, Agent, or Firm* — Cynthia S. Lamon; Lamon Patent Services

(57) ABSTRACT

A system for feeding and evacuation has a feeding tube in place into a subject's stomach cavity, having a Luer-Lock compatible female connector on an outboard end, a feed source, a unique Lopez valve having a conventional connector on one end and a male Luer-Lock connector on the other end in place of the conventional tapered connector, a suction tube coupled to a suction source, the suction tube having a connector compatible with the conventional connector of the conventional Lopez valve on an end away from (Continued)

the suction source. With the feeding tube connected to the feed source, nutrients are supplied to the subject through the feeding tube, and with the feed source disconnected, the body of the unique Lopez valve connected to the feed tube by the male Luer-Lock extension and to the suction tube, the subject's stomach cavity is exposed to suction controlled by the conventional Lopez valve.

1 Claim, 4 Drawing Sheets

(56) References Cited

U.S. PATENT DOCUMENTS

| | | | |
|---|---|---|---|
| 7,156,826 B2 * | 1/2007 | Ishii | A61M 39/223 604/523 |
| 9,101,742 B2 * | 8/2015 | Spera | A61M 31/00 |
| 10,105,529 B2 | 10/2018 | Ryan | |
| 2001/0001316 A1 * | 5/2001 | Nowakowski | A61L 24/0005 606/214 |
| 2002/0017328 A1 * | 2/2002 | Loo | F16K 11/085 137/625.47 |
| 2004/0054350 A1 * | 3/2004 | Shaughnessy | A61J 15/0003 604/535 |
| 2006/0025725 A1 | 2/2006 | Cassidy | |
| 2007/0129705 A1 * | 6/2007 | Trombley, III | A61M 39/12 604/523 |
| 2010/0168718 A1 * | 7/2010 | Bellisario | A61M 39/105 604/533 |
| 2012/0029481 A1 * | 2/2012 | Pech | A61M 39/10 604/533 |
| 2015/0246102 A1 * | 9/2015 | Margolin | A23L 29/06 424/94.6 |
| 2016/0354595 A1 * | 12/2016 | Gallagher | A61B 5/14546 |
| 2017/0203086 A1 * | 7/2017 | Davis | A61M 39/10 |

FOREIGN PATENT DOCUMENTS

| | | | | |
|---|---|---|---|---|
| WO | 2014/123658 A1 | 8/2014 | | |
| WO | WO-2020070044 A1 * | 4/2020 | | A61J 1/201 |

* cited by examiner

FEEDING TUBE MANAGEMENT

BACKGROUND OF THE INVENTION

1. Field of the Invention

The present invention is in the technical field of apparatus for intubation feeding and gastric suction, and methods for using such apparatus.

2. Description of Related Art

Both providing sustenance with feeding tubes and gastric suction to empty stomach contents in emergencies are well known processes in the art, and equipment is well known. It is known as well that patients being fed with a feeding tube may need to be intubated for gastric suction on occasion for various reasons. To do so it is necessary to remove (pull out) the feeding tube and then to insert an intubation tube. This is a hardship for the patient, extra close work for a nurse, is often painful, and may cause tissue damage in the throat and esophagus.

Feeding tubes, referred to in the art as Salem tubes, are rigid and are used for long-term feeding and are typically inserted down the throat. In an alternative method a gastrostomy tube (also called a G-tube) may be inserted through the abdomen into the stomach to bring nutritive material directly to the stomach. This one of the ways doctors can make sure kids who have trouble eating get the fluid and calories they need. A surgeon puts in a G-tube during a short procedure called a gastronomy.

What is clearly needed is apparatus and a method whereby feeding may be done through a tube and gastric suction may be accomplished through the same tube.

BRIEF SUMMARY OF THE INVENTION

The present invention, in one embodiment provides a system for both feeding and evacuation, comprising a feeding tube in place into a subject's stomach cavity, having a Luer-Lock compatible female connector on an outboard end. The system may also include a feed source, a conventional Lopez valve having a tapered connector on one end, and a suction tube coupled to a suction source, the suction tube having a connector compatible with a connector of the conventional Lopez valve on an end away from the suction source. Additionally, in this embodiment, a body of a Luer-Lock syringe is embodies at another outboard position of the Lopez valve, less the needle extension and the plunger, providing a connector with a male Luer-Lock extension on one end and a female opening on an opposite end.

In this embodiment, the feeding tube is connected to the feed source, nutrients are supplied to the subject through the feeding tube, and with the feed source disconnected, the body of the Luer-Lock syringe connected to the feed tube by the male Luer-Lock extension and to the conventional Lopez valve by the female open end to the tapered connection of the Lopez valve, and the conventional Lopez valve connected to the suction tube, the subject's stomach cavity is exposed to suction controlled by the conventional Lopez valve.

The Luer-Lock compatible connector on the outboard end of the feeding tube is a Y-Port with Luer-Lock compatible ports, in another embodiment.

A method for transitioning from feeding a subject through a feed tube into the subject's stomach cavity and evacuating the subject's stomach cavity is provided, comprising: a) with the feeding tube in place and connected to a feed source by an outboard end having a female Luer-Lock compatible connector, determining to change to evacuating the subject's stomach cavity; b) disconnecting the feed source from the feed tube at the female Luer-Lock compatible outboard connector, leaving the feed tube in place into the subject's stomach cavity; c) connecting a body of a Luer-Lock syringe stripped of a needle end and a plunger, to the female Luer-Lock compatible connector at the outboard end of the feed tube by the male end of the body of the Luer-Lock syringe, leaving the feed tube in place; and d) connecting the female opening at the opposite end of the body of the Luer-Lock syringe to a conventional Lopez valve by tapered connector of the Lopez valve; and finally connecting the Lopez valve to a suction tube connected to a suction source, wherein the suction tube coupled to the suction source by the body of the Luer-Lock syringe evacuates the subject's stomach cavity without removing the feed tube.

A further embodiment provides a system for both feeding and evacuation, comprising a feeding tube in place into a subject's stomach cavity, having a Luer-Lock compatible female connector on an outboard end, a feed source, a unique, novel, modified Lopez valve having a conventional connector on one end and a male Luer-Lock connector on the other end in place of the conventional tapered connector. A suction tube is then coupled to a suction source, the suction tube having a connector compatible with the conventional connector of the conventional Lopez valve on an end away from the suction source, characterized in that with the feeding tube connected to the feed source, nutrients are supplied to the subject through the feeding tube, and with the feed source disconnected, the body of the unique Lopez valve connected to the feed tube by the male Luer-Lock extension and to the suction tube, the subject's stomach cavity is exposed to suction controlled by the conventional Lopez valve.

Another method is provided transitioning from feeding a subject through a feed tube into the subject's stomach cavity and evacuating the subject's stomach cavity, comprising, with the feeding tube in place and connected to a feed source by an outboard end having a female Luer-Lock compatible connector, determining to change to evacuating the subject's stomach cavity. Disconnecting the feed source from the feed tube, is next in this embodiment, at the female Luer-Lock compatible outboard connector, leaving the feed tube in place into the subject's stomach cavity, then connecting a unique Lopez valve to the female Luer-Lock compatible connector at the outboard end of the feed tube by a male Luer-Lock extension on the unique Lopez valve. Finally, a connection is made between the unique Lopez valve to a suction tube connected to a suction source. In this embodiment, the suction tube is coupled to the suction source by the unique Lopez valve evacuates the subject's stomach cavity without removing the feed tube with suction controlled by the unique Lopez valve.

DETAILED DESCRIPTION OF THE INVENTION

A novel connector in an embodiment of the invention can be used or connected to a G tube or Salem tube, or other types of tubes in order to turn feeding tubes into suction tubes. This is helpful because a minor surgery must occur in the case of G tube use to insert a suction tube or to plug the G tube and insert the suction tube down a throat of a patient. Also, sometimes during gastronomic surgery, a suction tube must be inserted, if the feeding tube is in place, no substitution need occur, as the novel connector serves to connect the suction line to the feeding tube or tubes.

Figure 1:
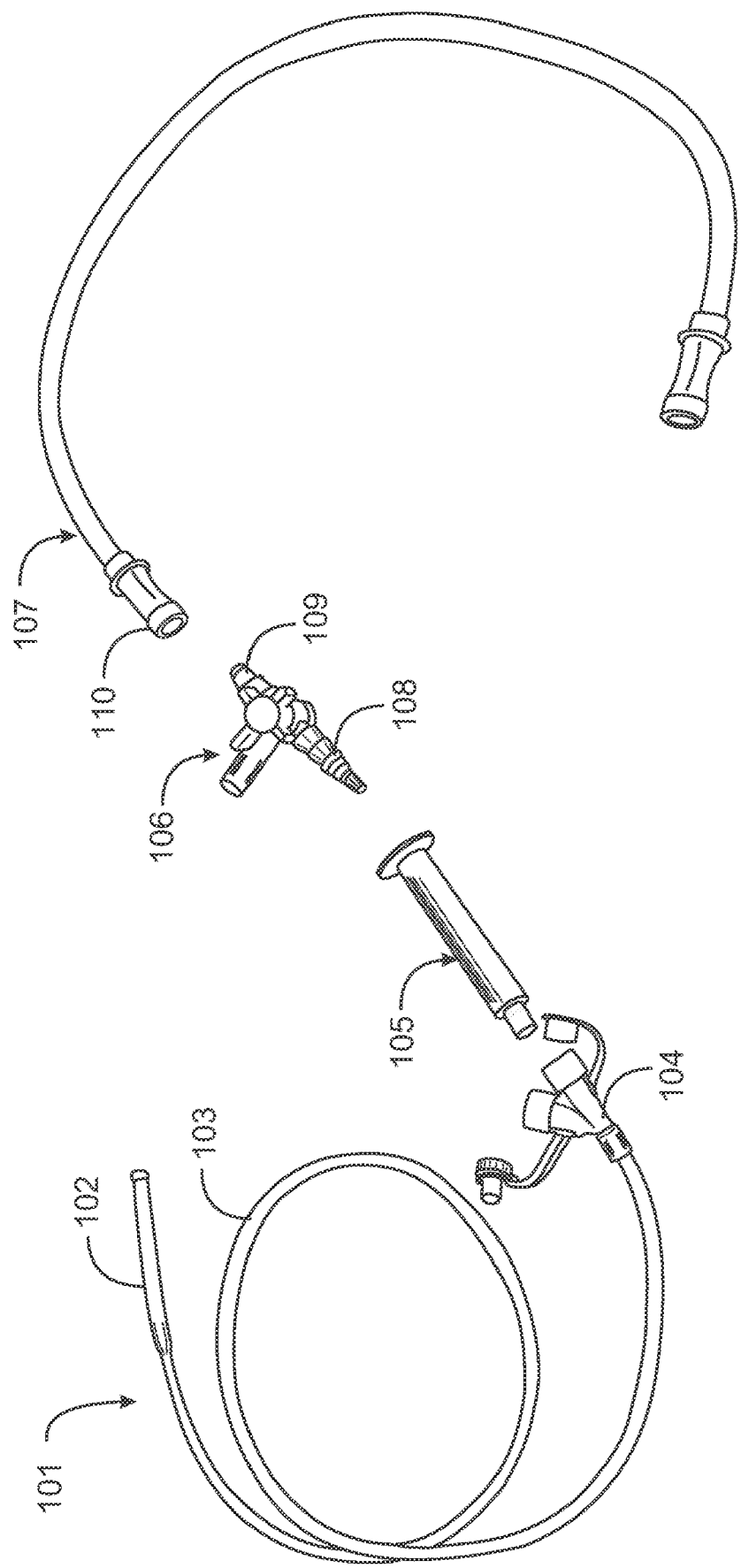
FIG. 1 is a comprehensive view of disassembled apparatus in an embodiment of the present invention.

FIG. 1 is a comprehensive view of disassembled apparatus in an embodiment of the invention. The overall apparatus comprises a feeding tube 101, which may be a nasogastric tube, inserted through the nasal cavity, or a Salem tube inserted directly into the stomach cavity through the abdominal wall. The feeding tube in this example has an end equipped with a Y-Port 104, allowing the feeding tube to be connected to one or two feeding bags (not shown). A novel connector 105 is an important component in embodiments of the invention. This element enables a user to disconnect a feed source from Y-Port 104 of feeding tube 101, and to connect instead a suction tube 107, enabling the user to apply suction by a suction source (not shown) through the suction tube to evacuate content from a subject's stomach without having to withdraw the feeding tube. Suction sources are well-known in the art and need not be described in detail in this specification.

As described above in the background section a big problem in use of feeding tubes is that, when it becomes necessary to evacuate the subject's stomach cavity, the feeding tube typically must be withdrawn first, and an intubation tube inserted. To avoid this serious problem the inventor discovered that a body of a common Luer-Lock syringe might be adapted to connect an in-place feeding tube to a suction tube coupled to a suction source to evacuate the subject's stomach cavity without having to remove the feeding tube.

In this example a Luer-Lock syringe is stripped of its needle section and the plunger is withdrawn and removed leaving the body of the syringe as connector 105, with a male Luer-Lock extension on one end. The male end of body 105 of the Luer-Lock syringe is compatible to connect directly to Y-Port 104 of feeding tube 101, and the female plunger end is compatible to connect to a medical Lopez valve 106, which has a tapered N G Tube connection 108 which is compatible to insert into the female end of body 105. The Lopez valve connects by end 109 to connector 110 on an end of the suction tube away from the suction source. The Lopez valve adds functionality enabling a user to start, stop and control flow in evacuating a subject's stomach through the still in-place feeding tube. The system may be used, however, without the Lopez valve.

The novel connector may be connected to a G tube or Salem tube, or other type of tubes in order to repurpose in-place feeding tubes into suction tubes. This is novel and useful because a minor surgery must occur in the case of G tube use to insert a suction tube or plug the G tube and insert the suction tube down a throat of a patient. Also, sometimes during gastronomic surgery, a suction tube must be inserted. If the feeding tube is in place, no substitution need occur, as the novel connector serves to connect the suction line to the feeding tube(s).

Figure 2:
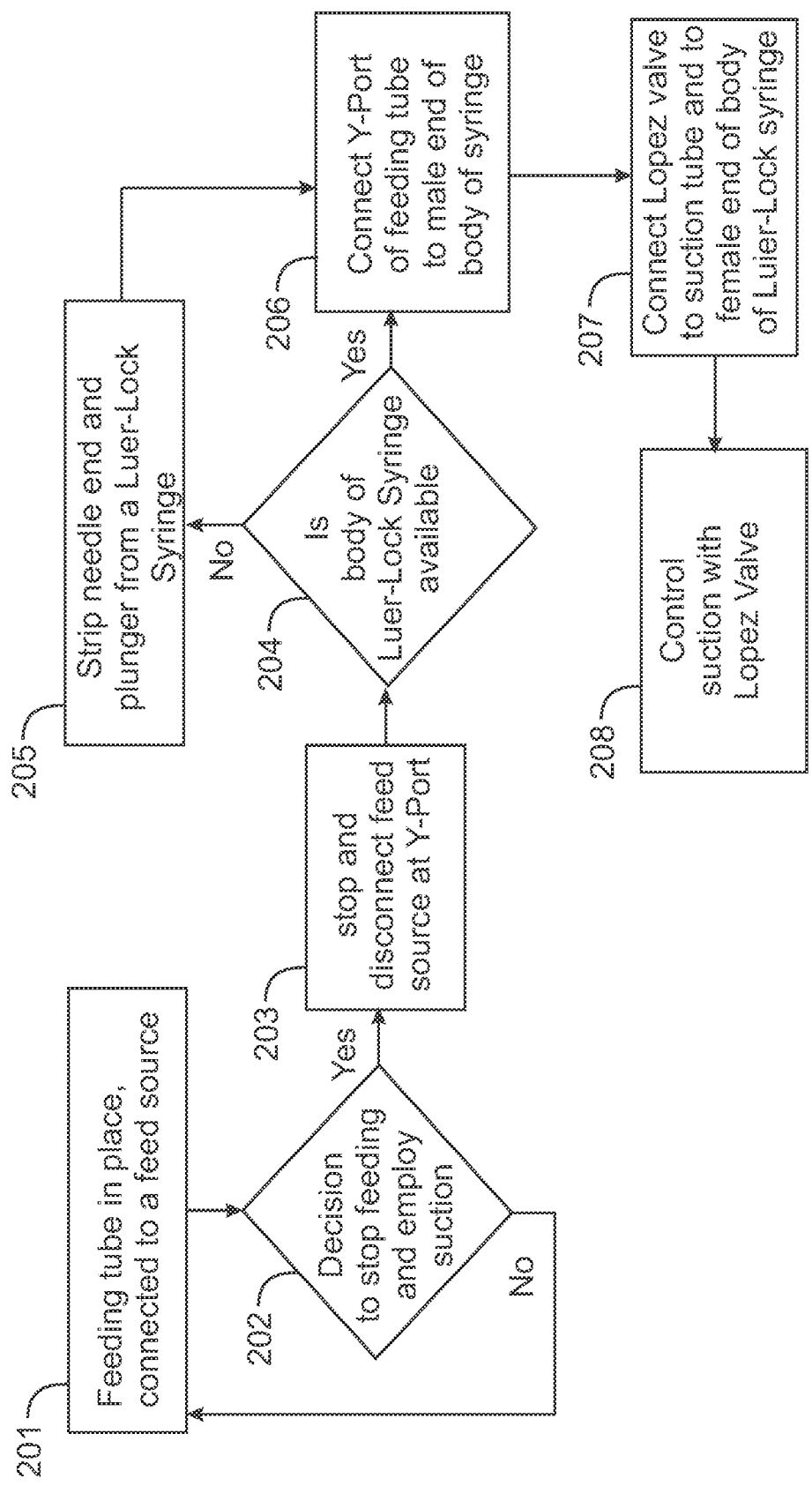
FIG. 2 is a flow diagram of a procedure in an embodiment of the invention.

FIG. 2 is a flow chart illustrating a process in an embodiment of the present invention. This process starts at step 201 with a feeding tube in place and functional in a subject. At step 202 it is determined whether or not a decision has been made to stop feeding and to employ suction. If No, control goes back to step 201. If Yes, the feed source is disconnected from the feed tube at step 203. At step 204, after the feed source is disconnected from the fed tube at the Y-Port, it is determined if a body of a Luer-Lock Syringe is available to be used as a connector. If no, a Luer-Lock syringe is obtained at step 205 and the needle end and plunger are removed, leaving the body with a male Luer-Lock end.

If at step 204 the Luer-Lock body is available, or a body is made available at step 205, at step 206 the Y-Port of the feeding tube is connected to the male end of the body of the syringe. At step 207 a Lopez valve is connected to the suction tube and to the female end of the body of the Luer-Lock syringe. At step 208 the Lopez valve as sued to control suction.

Figure 3:
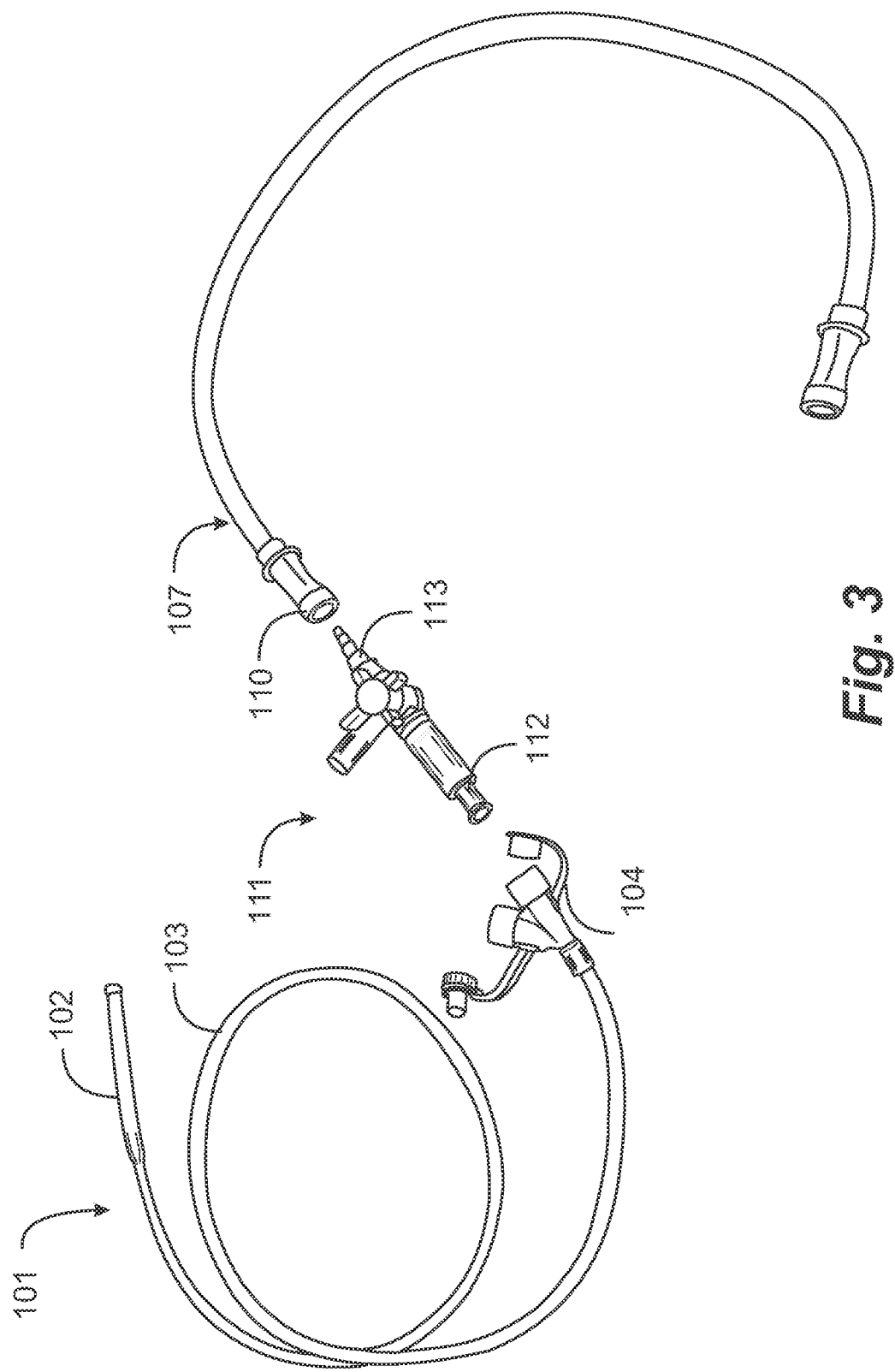
FIG. 3 is a comprehensive view of disassembled apparatus in an alternative embodiment of the present invention.

FIG. 3 is a comprehensive view of disassembled apparatus in an alternative embodiment of the present invention. The elements of the apparatus are the same except that the Lopez valve 106 is replaced with a new and unique Lopez valve 111 with a Luer-Lock male end 112 and an end 113 the same as end 109 of the conventional Lopez valve of FIG. 1. In this embodiment the body of a Luer-Lock syringe is no longer needed.

Figure 4:
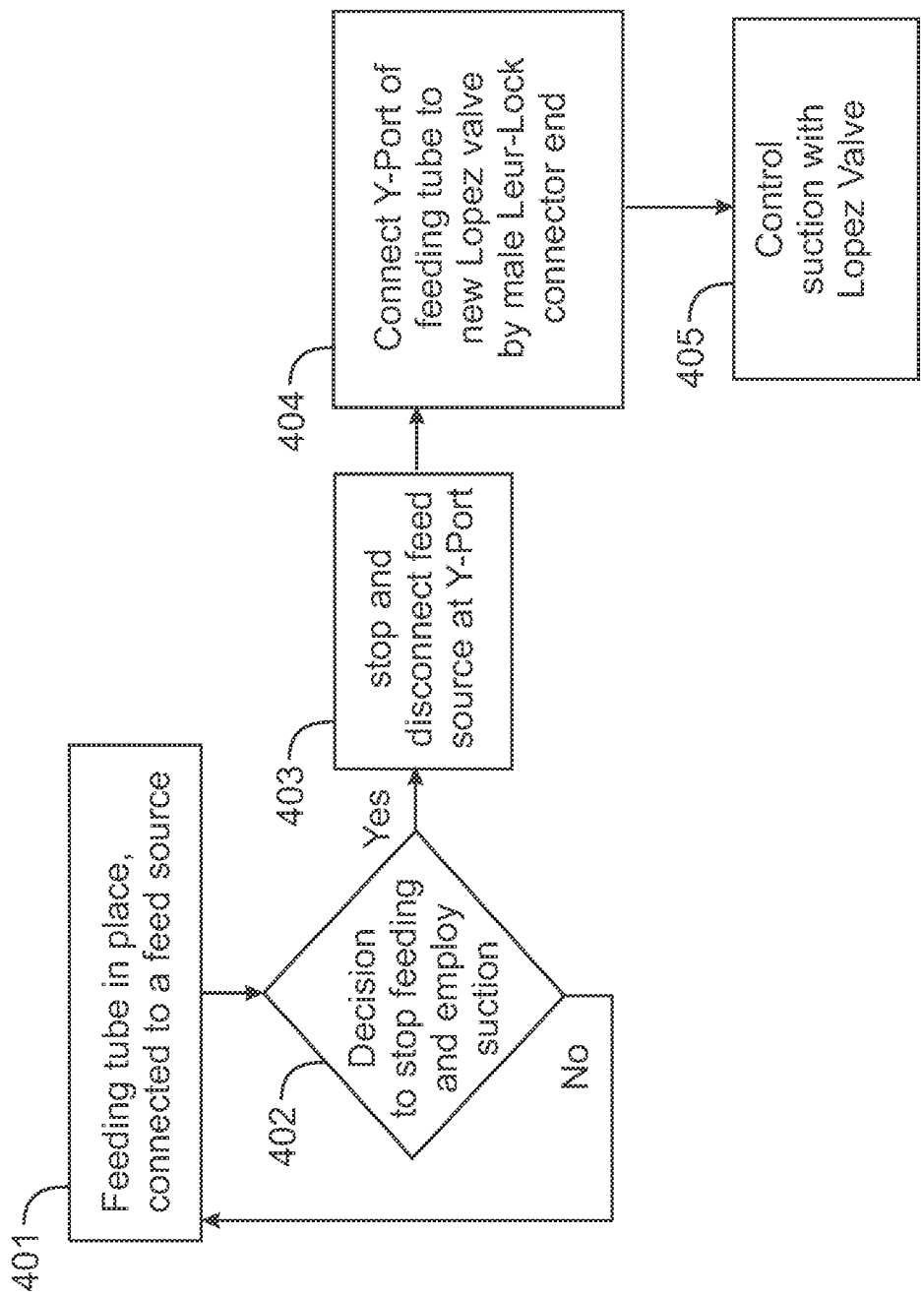
FIG. 4 is a flow diagram of a procedure in the embodiment of the invention with the apparatus of FIG. 3.

FIG. 4 is a flow diagram of a procedure in the embodiment of the invention incorporating the apparatus of FIG. 3. At step 401 a feeding tube is in place connected to a feed source. At step 402 it is determined to stop feeding and to employ suction. If the determination is made, at step 403 feeding is stopped and the feed source is disconnected at the Y-Port. At step 404 the Y-Port of the feeding tube is connected to the male Luer-Lock port of the new Lopez valve, and at step 405 suction is controlled with the new Lopez valve.

A person with skill in the medical arts will understand that the illustrations and descriptions in this specification and figure set are exemplary only, and apparatus and function in embodiments of the invention are not limited to just these specific examples. There are a variety of alterations that might be made without departing from the scope of the invention. One such variation is the use, or absence of the Lopez medical valve. Use of the valve adds control to the suction phase of the process but is not essential to the invention. Various sorts and lengths of feeding tubes may be employed in embodiments of the invention and not all are specifically called out in these descriptions. Different sorts of suction tubes and suction sources may be used as well in different variants of the invention. The scope of the invention is limited only by the claims.

The invention claimed is:

1. A method for transitioning from feeding a subject through a feed tube into the subject's stomach cavity and evacuating the subject's stomach cavity, comprising:
   with the feeding tube in place and connected to a feed source by an outboard end having a female Luer-Lock compatible connector, determining to change to evacuating the subject's stomach cavity;
   disconnecting the feed source from the feed tube at the female Luer-Lock compatible outboard connector, leaving the feed tube in place into the subject's stomach cavity;

providing a Luer syringe connector by removing a needle and plunger from a body portion of a Luer-Lock syringe, the body portion including a male Luer connector on one end and a female connector on an opposing end;

connecting a conventional tapered connector of a unique three-way stopcock to the female connector of the Luer syringe connector;

connecting the male Luer connector to the female Luer-Lock compatible connector on the feeding tube, thereby leaving the feeding tube in place, and connecting the unique three-way stopcock to a suction tube connected to a suction source enabling evacuation of the subject's stomach cavity without removing the feed tube from the subject's stomach and suction is controlled by the unique three-way stopcock.

* * * * *